(12) United States Patent
Vincent et al.

(10) Patent No.: US 6,444,231 B2
(45) Date of Patent: *Sep. 3, 2002

(54) USE OF TRIAQUA-$\mu$3-OXOHEXAKIS-$\mu$-PROPIONATOTRICHROMIUM(1+), [$CR_3O$ $(O_2CCH_2CH_3)_6(H_2O)_3$]$^+$, AS A NUTRITIONAL SUPPLEMENT OR IN TREATMENT OF MEDICAL CONDITIONS

(75) Inventors: John B. Vincent; Catherine M. Davis, both of Tuscaloosa, AL (US)

(73) Assignee: University of Alabama, Tuscaloosa, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/760,856

(22) Filed: Jan. 17, 2001

Related U.S. Application Data

(62) Division of application No. 09/163,005, filed on Sep. 30, 1998, now Pat. No. 6,197,816.

(51) Int. Cl.$^7$ .......................... A61K 33/24; A61K 31/28
(52) U.S. Cl. ........................................ 424/655; 514/505
(58) Field of Search ........................... 424/655; 514/505

(56) References Cited

U.S. PATENT DOCUMENTS 5,872,102 A    2/1999  Vincent et al.
6,149,948 A  * 11/2000 Vincent ....................... 424/655

OTHER PUBLICATIONS

T. Yosida et al., "High Magnetic Field Study of Chromium Trimer Complexes Below 1 K", *Journal of the Physical Society of Japan*, Apr. 1988, vol. 57, No. 4, pp. 1428–1434.

V. Weinland et al., "Über Verbindungen mit Trichromi-Hexapropionato–(Formiato)–Fluoro–Komplexen", pp. 285–302, 1930.

N. Mirsky et al., "Chromium in Biological Systems, I. Some Observations on Glucose Tolerance Factor in Yeast", *Journal of Inorganic Biochemistry*, 1980, vol. 13, pp. 11–21.

H. Nishimura et al., "Anomalous G–Value of a Cr–Trimer Complex, Cr–Propionate $\{Cr_3O(C_2H_5COO)_6(H_2O)_3\}$-$NO_3 2H_2O$", *Journal of the Physical Society of Japan*, Jan. 1985, vol. 54, No. 1, pp. 395–399.

Antsyshkina, "Crystal Structure and Several . . . ", *Zhurnal Neorganicheskoii KHIMII*, 1987, vol. 32, No. 12, pp. 2928–2932.

A. v.d. Bergen et al., "Electrospray Mass Spectrometric Study of $[M_3O(RCOO)_6L_3]^+$ Cations (M=Cr, Fe; $L=H_2O$, MeOH, py)", *Inorg. Chem.*, 1993, vol. 32, pp. 3408–3411.

M. Honda et al., "Electron Spin Resonance in Cr–Trimer Complexes", *Journal of the Physical Society of Japan*, Oct. 1992, vol. 61, No. 10, pp. 3773–3785.

A. Earnshaw et al., "Chemistry of Polynuclear Compounds. Part VI* Magnetic Properties of Trimeric Chromium and Iron Carboxylates", *J. Chem. Soc. (A)*, 1966, pp. 1656–1663.

M. Glass et al., "Nuclear Magnetic Resonance Studies of Multinuclear Chromium Assemblies", *Polyhedron*, 1993, vol. 12, No. 2, pp. 133–140.

Yuan et al., "Study on the Dual MU . . . ", *Hua Hsueh Hsueh Pao. Acta Chimica Sinica*, 1993, vol. 51, No. 6, pp. 579–585.

(List continued on next page.)

*Primary Examiner*—Russell Travers
*Assistant Examiner*—Shengjun Wang
(74) *Attorney, Agent, or Firm*—Oblon, Spivak, McClelland, Maier & Neustadt, P.C.

(57) ABSTRACT

Methods of using the chromium(III) complex represented by the formula $[Cr_3O(O_2CCH_2CH_3)_6(H_2O)_3]^+$ as a nutritional supplement, and for treating medical disorders associated with chromium deficiency. Nutritive and pharmaceutical compositions containing this chromium(III) complex are also provided.

10 Claims, 5 Drawing Sheets

OTHER PUBLICATIONS

R. Weinland et al., "Über Salze Einer Grü nen und Einer Violetten Propionato–Chrombase", *Zeitschrift fur Anorganische Chemie*, 1911, vol. 69, pp. 158–178.

J. Vincent, "Heterotrinuclear Carboxylates of Chromuim(III) and Iron(III): Mixtures or Pure Compounds?", *Inorg. Chem.*, 1994, vol. 33, pp. 5604–5606.

Zelentsova et al., "Magnetism of Chromium(III) and Iron(III) . . . ", 1975, vol. 1, No. 2, pp. 194–201.

Szymanska–Buzar et al., "MU.3–Oxotrimetalcarboxylates of 3D Elements . . . ", *Koordinatsionnaia Khimiia*, 1976, vol. 2, No. 9, pp. 1172–1191.

J. K. Speetjens et al., "The Nutritional Supplement Chromium(III) Tris(Picolinate) Cleaves DNA", *Chemical Research in Toxicology*, Jan. 28, 1999, vol. 12, No. 6, pp. 483–487.

J. Vincent, "Mechanism of Chromium Action: Low–Molecular–Weight Chromium–Binding Substance", *Journal of the American College of Nutrition*, 1999, vol. 18, No. 1, pp. 6–12.

C. Davis et al., "Synthetic Multinuclear Chromium Assembly Activates Insulin Receptor Kinase Activity: Functional Model for Low–Molecular–Weight Chromium–Binding Substance", *Inorganic Chemistry*, 1997, vol. 36, No. 23, pp. 5316–5320.

R. Anderson et al., "Dietary Chromium Effects on Tissue Chromium Concentrations and Chromium Absorption in Rats", *The Journal of Trace Elements in Experimental Medicine*, 1996, vol. 9, pp. 11–25.

M. Morita et al., "$N_2$ Laser–Excited Luminescence of Antiferromagnetically Coupled Trinuclear Chromium(III) Complexes", *International Journal of Quantum Chemistry*, 1980, vol. XVIII, pp. 625–631.

G. Fu et al., "Fast Atom Bombardment Mass Spectra of Trinuclear.MU.3–OXO–Carboxylato Complexes of Chromium", *Jiegou Huaxue (J. Struct. Chem.)*, 1990, vol. 9 No. 4 w/English Abstract.

M. K. Johnson et al., "Vibrational Spectra of Carboxylato Complexex–III. Trinuclear 'Basic' Acetates and Formates of Chromium(III), Iron(III) and Other Transition Metals", *Spectrochimica Acta.*, 1981, vol. 37A, No. 11, pp. 995–1006.

* cited by examiner

US 6,444,231 B2

USE OF TRIAQUA-µ3-OXOHEXAKIS-µ-PROPIONATOTRICHROMIUM(1+), [CR$_3$O (O$_2$CCH$_2$CH$_3$)$_6$(H$_2$O)$_3$]$^+$, AS A NUTRITIONAL SUPPLEMENT OR IN TREATMENT OF MEDICAL CONDITIONS

This application is a Divisional of U.S. application Ser. No. 09/163,005, filed on Sep. 30, 1998, now allowed U.S. Pat. No. 6,197,816.

BACKGROUND OF THE INVENTION

1. Field of the Invention

The present invention relates to methods of using the chromium(III) complex represented by the formula [Cr$_3$O (O$_2$CCH$_2$CH$_3$)$_6$(H$_2$O)$_3$]$^+$ as a nutritional supplement, and for treating medical disorders associated with chromium deficiency. The invention also relates to nutritive and pharmaceutical compositions containing this chromium(III) complex.

2. Background of the Invention

The biologically-active, naturally-occurring oligopeptide low-molecular-weight chromium-binding substance (LMWCr) has been found to activate the insulin-dependent tyrosine protein kinase activity of insulin receptor (IR) approximately eightfold with a dissociation constant of circa 250 pM.[1] This activity is directly proportional to the Cr content of the oligopeptide (being maximal at four chromic ions per oligopeptide), while substitution of chromium with metal ions commonly associated with biological systems results in inactivating the oligopeptide. Similarly, LMWCr has been reported to activate a membrane-associated phosphotyrosine phosphatase; this activation also requires four chromic ions per oligopeptide to be maximal, while chromic ions could not functionally be replaced with other transition metal ions.[2] A role for LMWCr in amplification of insulin-signaling has been postulated.[1,3] Chromium is mobilized from the blood and taken up by insulin-dependent cells in response to insulin.[4] LMWCr is maintained in its apo form[5] but possesses a large chromic ion binding constants(s) as it is capable of removing chromium from Cr-transferring.[5,6] The holo LMWCr is then capable of stimulating IR kinase activity, amplifying the signal of insulin into the insulin-dependent cells. An association between chromium and insulin-dependent glucose and lipid metabolism has been reported for nearly four decades;[7] however, only recently since procedures for isolation of quantities of LMWCr suitable for kinetic and spectroscopic studies have been developed[3] has progress been made in understanding the association on a molecular level.

An association between the essential nutrient chromium and adult-onset diabetes has also been postulated.[8] Most recently Anderson and coworkers found improved glycemic control for 180 adult-onset diabetic patients following chromium supplementation,[9] while Ravina and Slezack using 138 adult-onset diabetic patients found reduced insulin requirements.[10] Unfortunately, the form of chromium used as a dietary supplement in these studies, chromium(III) picolinate, has been found to cause chromosome damage.[11] This suggests that a new form of chromium for use as a dietary supplement and as part of a potential treatment for adult-onset diabetes is required.

LMWCr would appear to be a possibility. It has a high LD$_{50}$[6] and is biologically active, opposed to chromium picolinate and glucose tolerance factor (a material isolated from acid-hydrolyzed Brewer's yeast extracts) which serve only as sources of readily absorbable chromium.[2] However, LMWCr is susceptible to hydrolysis under acidic conditions[14] and consequently could not be taken orally without degradation.

Despite the apparent significance of Cr, as much as ninety percent of the American population and half of the population of developed nations fail to intake the daily recommended safe and adequate quantities of Cr.[13] Accordingly, there remains a need for improved chromium-containing dietary supplements.

SUMMARY OF THE INVENTION

The present invention is based on the discovery that the chromium(III) complex having the formula [Cr$_3$O (O$_2$CCH$_2$CH$_3$)$_6$(H$_2$O)$_3$]$^+$ (complex (1)) activates tyrosine kinase activity, e.g., insulin receptor tyrosine kinase activity. Complex (1) catalyzes the transfer of the gamma phosphate of ATP to tyrosine residues of proteins or polypeptides. The complex can thus be used as a biomimetic, i.e., a synthetic enzyme, in applications where generation of phosphotyrosine is desired. As phosphorylation of tyrosine is an essential step in many signal transduction pathways such an artificial tyrosine protein kinase may have numerous medicinal applications. In addition, the complex is biologically active, stable under acidic conditions, and readily and inexpensively synthesized.

Complex 1 may be used a nutritive supplement for augmenting the diets of animals with chromium. The cationic complex may also be used to treat medical conditions associated with a decrease in chromium and/or responsive to enhanced bodily levels of chromium, e.g., adult-onset diabetes and other conditions associated with glucose intolerance, and cardiovascular disorders.

Complex 1 may be used alone for these purposes, or may be combined with excipients and/or other animal nutrients to provide a nutritive composition for bolstering chromium levels. The complex may also be combined with additional pharmaceutical agents.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

Figure 1:
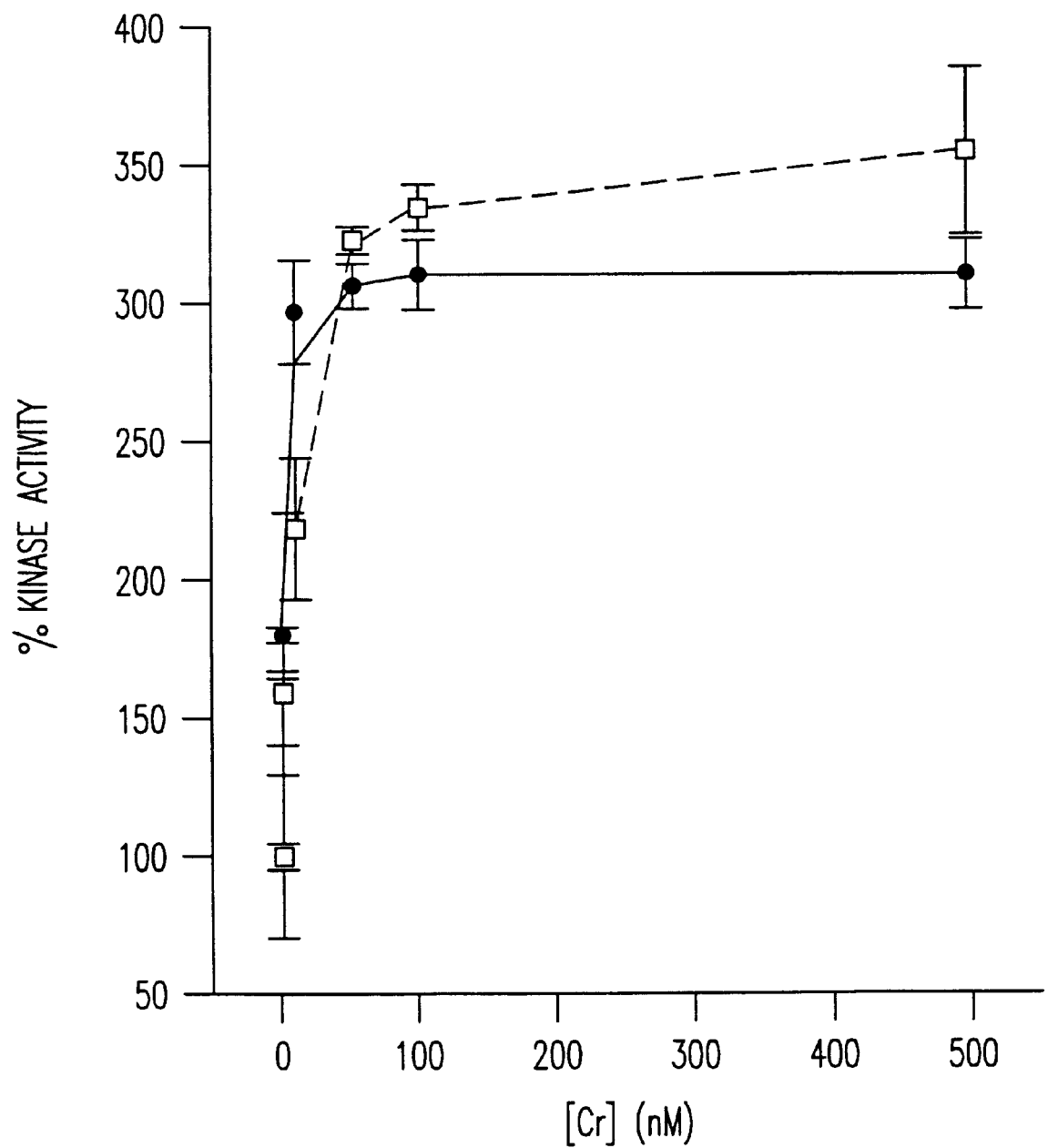
FIG. 1: Activation of protein tyrosine kinase activity of the isolated active site fragment of the β-subunit of insulin receptor by bovine liver LMWCr (open squares) and [Cr$_3$O (O$_2$CCH$_2$CH$_3$)$_6$(H$_2$O)$_3$]NO$_3$ (solid circles) using a fragment of gastrin (0.75 mM) as substrate in the presence of 100 nM insulin. The line is the best curve fit giving for LMWCr a dissociation constant of 133 pM and for [Cr$_3$O (O$_2$CCH$_2$CH$_3$)$_6$(H$_2$O)$_3$]$^+$ a dissociation constant of 1.00 nM.

Chromium complex 1 can be used to supplement the diet of animals with chromium. The complex may be administered to the patient by injection, I.V. or oral administration as, for example, an aqueous solution or suspension. These solutions and suspensions may contain all of the customary additives well known to those of skill in the art, e.g., buffering agents, salts (e.g., NaCl), sugars (e.g., glucose and lactose), etc. Alternatively, the complex can be formulated into a solid dosage form, such as a tablet, pill, capsule or caplet, suitable for oral ingestion. The daily dosage of complex 1 may vary over a wide range, such as 5 to 600 micrograms of Cr per day, including all specific values and subranges therebetween.

Complex 1 may be used as a chromium dietary supplement to maintain good health and nutrition. Complex 1 may also be used to treat medical conditions which are associated with chromium deficiency or conditions which are ameliorated by increasing bodily levels of chromium.

Complex 1 activates insulin receptor protein tyrosine kinase activity. Accordingly, administering the complex may be used as a method of treating adult-onset diabetes. In addition, it is known that cardiovascular diseases are associated with chromium deficiencies. Accordingly, cardiovascular diseases may be effectively treated by administering complex 1 to patients.

Complex 1 may also be used as a component of an animal nutrient composition. Such a composition contains chromium complex 1 and at least one pharmacologically acceptable excipient. Suitable excipients are well-known and include diluents, disintrgrators, binders and lubricants (glidants). Specific examples include, for example, celluloses, gelatins, starches, polysorbate 80, oils (e.g., peanut oil, fish liver oil). Preferably, the nutritive composition is made to U.S. Pharmacopiea quality, purity and potency standards. The nutrient composition is preferably in the form of a solid. For a description of solid compositions, see Pharmaceuticals, Kirk-Othmer Encyclopedia of Chemical Technology, Fourth Edition, Volume 18, pp. 480–510, incorporated herein by reference The nutritive composition may also contain at least one additional animal nutrient. As used herein the term "animal nutrient" refers to compounds and substances which are recognized to maintain and regulate bodily functions. Specific examples of additional animal nutrients include vitamins (e.g., vitamin A, beta carotene, vitamin $B_1$, vitamin $B_2$, vitamin $B_6$, vitamin $B_{12}$, vitamin C, vitamin D, vitamin E, vitamin K), minerals (e.g., calcium, iron, copper, selenium, zinc, magnesium), enzyme cofactors, iodine, phosphorous, folate, biotin, and niacin.

Complex 1 may also be used as a component of a pharmaceutical composition. Such a composition contains chromium complex 1 and at least one additional pharmaceutical agent. As used herein the tern "pharmaceutical agent" refers to compounds and substances which are recognized to as treatment and or therapies for a disease state, e.g., drugs. Specific examples of the pharmaceutical agent include insulin and other anti-diabetes medications. For a discussion of insulin and other antidiabetes medicines, see Insulin and Other Antidiabetic Agents, Kirk-Othmer Encyclopedia of Chemical Technology, Fourth Edition, Volume 14, pp. 662–676, incorporated herein by reference. The pharmaceutical composition may also contain any of the well-recognized excipients discussed above. The pharmaceutical composition is preferably in a solid dosage form as discussed above.

As used herein, the terms "animal" and "patient" include humans and non-human animals. A particularly preferred group of non-human animals are mammals (such as farm animals, cats and dogs).

Since 1 is a cation, the complex will, of course, be in the form of a salt with an anion. The anion should be non-toxic when used in the methods according to the present invention, i.e., the anion is pharmcologically acceptable. The anion is preferably the salt of a pharmcologically acceptable inorganic or organic acid. Specific examples of suitable anions include nitrate, sulfate, chloride, bromide, iodide, phosphate, Having generally described this invention, a further understanding can be obtained by reference to certain specific examples which are provided herein for purposes of illustration only and are not intended to be limiting unless otherwise specified.

EXAMPLES

Materials and Methods

LMWCr, $[Cr_3O(O_2CCH_3)_6(H_2O)_3]Cl$, and $[Cr_3O(O_2CCH_2CH_3)_6(H_2O)_3]NO_3$ LMWCr was available from previous work and contained 3.6–4.0 chromium per oligopeptide.[1-3] $[Cr_3O(O_2CCH_3)_6(H_2O)_3]Cl$ (2) and $[Cr_3O(O_2CCH_2CH_3)_6(H_2O)_3]NO_3$ (1) were prepared as previously described.[15,16] Oligopeptide concentrations were assayed using the fluorescamine procedure of Undenfriend and coworkers[17] with glycine as a standard. chromium concentrations were measured using the diphenylcarbizide method[18] and the method of standard additions to minimize any potential matrix effects. For all kinetic experiments, solutions of LMWCr, 1, and 2 were prepared by dilutions from more concentrated stock solutions. The chromium(III)-amino acid mixture was prepared by mixing chromic nitrate, aspartate, glutamate, glycine, and cysteine in a 4:2:4:2:2 ratio in water, followed by heating at 37° C. for thirty minutes to allow complexes to form. To obtain proper concentrations of this mixture (in terms of Cr concentration) for kinetic experiments, serial dilutions were prepared.

Purification of Isolated Adipocytes and Adipocytic Membranes

Fat cells from male Sprague Dawley rats were isolated using the procedures of Rodbell[19] and Anderson et al.[20] with modifications.[2] Three rats (not kept on a Cr-deficient diet) were sacrificed by decapitation, and their epididymal fat pads removed. Rat adipocytes were washed with 1% bovine serum albumin (BSA). 50 mM Hepes, pH 7.4 buffer containing 10 μg/mL leupeptin and 5 μg/mL aprotinin. Cells were homogenized with a manual teflon homogenizer and frozen and thawed five times. The lipid layer was removed, and the cell homogenate was centrifuged for one hour at 40,000 g. The supernatant was removed, and the pellet was suspended in Hepes buffer and used as the source of membrane phosphatase and kinase activity. Protein concentrations were analyzed using the BCA method (Pierce Chemical Co.) with BSA as standard.

Phosphotyrosine Phosphatase Activity p-nitrophenyl phosphate (p-NPP) was used to determine the amount of PTP activity using the method of Li et al.[21] The assay used 5 mM substrate in 0.05M Tris, pH 7.5, unless noted. Activation of PTP activity by LMWCr and other Cr-containing species was examined as described by Davis et al.[2] Solutions of LMWCr, 1,2, and the Cr-amino acid mixture were incubated with the enzyme for fifteen minutes at 37° C. before initiation of the reaction. Hydrolyses proceeded for one hour at 37° C. The extent of hydrolysis was determined at 404 nm ($\epsilon=1.78\times10^4 M^{-1}cm^{-1}$).

Phosphotyrosine Kinase Activity

Phosphotyrosine kinase activity was measured using a protein tyrosine kinase assay kit (Boehringer Mannheim) which uses an anti-phosphotyrosine antibody to recognize phosphotyrosine. A fragment of gastrin (amino acids 1–17) which has been biotinylated so it can be immobilized to streptavidin-coated microtiter plates (Boehringer Mannheim) was used as the substrate. The assays were performed in 50 mM Tris, pH 7.4 containing 0.75 mM APT and 7.5 mM $MgCl_2$ at 37° C. for 75 minutes as previously described[1] unless otherwise noted. The membrane fragments which contain phosphotyrosine themselves were removed from the reaction was terminated with EDTA by Microcon 30 or Microcon 50 microconcentrators (Amicon), and ammonium vanadate was used as a phosphatase inhibitor. Contributions to the assay by the addition of metal-containing materials were determined by measuring the background absorbency of the assay in the absence membranes, and these contributions were subtracted from all data Bovine pancreas insulin was from Sigma. Isolated kinase active site fragment from he beta subunit of human insulin receptor (residues 941–1343) was obtained from Stratagene and diluted with 50 mM Tris, pH 7.4; the fragment does not require activation of the kinase activity by added insulin. Five units of IR fragment were used in kinetic assays; a unit of activity is defined as the picomoles of phosphate incorporated/minute/μL of kinase as received from the manufacturer. Recombinant human insulin-like growth factor-1 (IGF-1) was obtained from Sigma and reconstituted with 10 mM HCl.

Miscellaneous

All visible spectroscopic measurements were obtained with a Shimadzu UV-160A diode array spectrophotometer. Fluorescence measurements were made with a Perkin-Elmer 204 fluorescence spectrophotometer. $^1H$ NMR were obtained using a Bruker AM-360 spectrometer at circa 23° C. Chemical shifts are reported on the δ scale (shifts down field are positive) using solvent protio-impurity as a reference. Curve-fitting was performed using SigmaPlot (Jandel Scientific). All kinetic experiments were performed in triplicate. Errors are presented throughout including all tables and graphs as the standard deviations (1σ) of the triplicate analyses. Similarly, all Cr and LMWCr concentration determinations were made in triplicate. Doubly deionzed water was used in all operations; plasticware was used whenever possible.

RESULTS AND DISCUSSION

The binding of insulin to the alpha subunit of insulin receptor results in tyrosine autophosphorylation of the beta subunit of the receptor, transmitting the signal of the hormone insulin into a cell; autophosphorylation activates the kinase in the beta subunit which catalyzes phosphorylation of other proteins.[22] This kinase activity is potentiated by the oligopeptide LMWCr. Using isolated IR, potentiation of IR tyrosine protein kinase activity by LMWCr has been found to require insulin and is prevented when the insulin binding site of the external alpha subunit is blocked.[1] However, the binding site on IR for LMWCr is unknown. However, studies with a catalytically active fragment (residues 941–1343) of the beta subunit of the human enzyme indicate that the effect of LMWCr on kinase activity is associated with this fragment. As shown in FIG. 1, addition of LMWCr to the fragment results in an approximately three fold activation of the kinase activity. Fitting the curve to a hyperbolic equation gives a dissociation constant for LMWCr of 133 pM, very similar to the dissociation constant found for the interaction of LMWCr with isolated rat insulin receptor (250 pM).[1] The threefold activation is significantly less than that observed with isolated receptor (approximately eightfold),[1] but this may be associated with small structural differences between the fragment and the entire receptor protein. The results suggest that LMWCr may associate with the kinase active site of the insulin receptor.

Insulin receptor is part of a family of receptor proteins which includes the insulin-like growth factor receptors.[23] All these receptors are disulfide-bound heterotetramers of alpha and beta subunits. Ligand (insulin or insulin-like growth factors) presumably cause a conformational change in the preformed receptors, resulting in receptor activation. To examine the specificity of LMWCr, the effects of the oligopeptide on IGF-1 receptors was probed. The kinase activity of rat adipocytic membrane fragments in the presence of 100 nM IGF-1 is more than doubled by the addition of LMWCr (FIG. 2) with a dissociation constant of 507 pM. In contrast, in the presence of 100 nM insulin kinase activity has previously been shown using the same fragment of gastrin as substrate to be increased three and one-half times by LMWCr with a similar dissociation constant of 875 pM.[1] [In the absence of added hormone, LMWCr has no detectable effect on the membrane kinase activity.][1] Thus, LMWCr potentiates both members of the IGF receptor family.

Given this novel role in the amplification of signal transduction for LMWCr and its rather simple composition (carboxylate-rich oligopeptide binding four chromic ions),[3,5] the possibility of identifying a functional model for LMWCr was examined. Such a model would be required to be soluble and stable in aqueous solution, be well characterized, and contain a carboxylate-supported multinuclear chromic assembly.[3] Fortunately, a review of the literature revealed a number of trinuclear and tetranuclear Cr(III) carboxylate assemblies;[24,25] however, few were soluble in water. Based on these requirements, two were chose: $[Cr_3O(O_2CCH_2CH_3)_6(H_2O)_3]^{+1}$ and $[Cr_3O(O_2CCH_3)_6(H_2O)_3]^{+2}$. Both of these complexes possess a basic carboxylate type structure[25] comprised of a planar triangle of chromic ions with a central $\mu_3$-oxide. Each set of two chromic ions is bridged by two carboxylates ligands, while six coordination about the chromium centers is completed by a terminal aquo ligand.

The cation $[Cr_3O(O_2CCH_2CH_3)_6(H_2O)_3]^{+1}$ is a well characterized species. Its preparation was first described in 1911, although the formula was proposed as a hydrate salt of $[Cr_3(O_2CCH_2CH_3)_6(OH)_2]^{+}.^{26}$ A similar synthesis of a variety of salts of the cation (still with the wrong formulation) was reported in 1930.[27] The cation, which was originally characterized only by its color and elemental analysis, has subsequently been characterized by variable temperature magnetic susceptibility measurements,[1,6,28] electronic spectroscopy,[28] luminescence spectroscopy,[29] infrared spectroscopy and X-ray crystallography (of the nitrate salt),[30] ESR,[31] fast atom bombardment and electrosprary mass spectrometry,[32] and NMR.[33] The cation $[Cr_3O(O_2CCH_3)_6(H_2O)_3]^{+2}$ has been more exhaustively studied and has served as a model upon which theories of the magnetic interactions between multiple paramagnetic centers were tested (reviewed in ref. 25).

Figure 2:
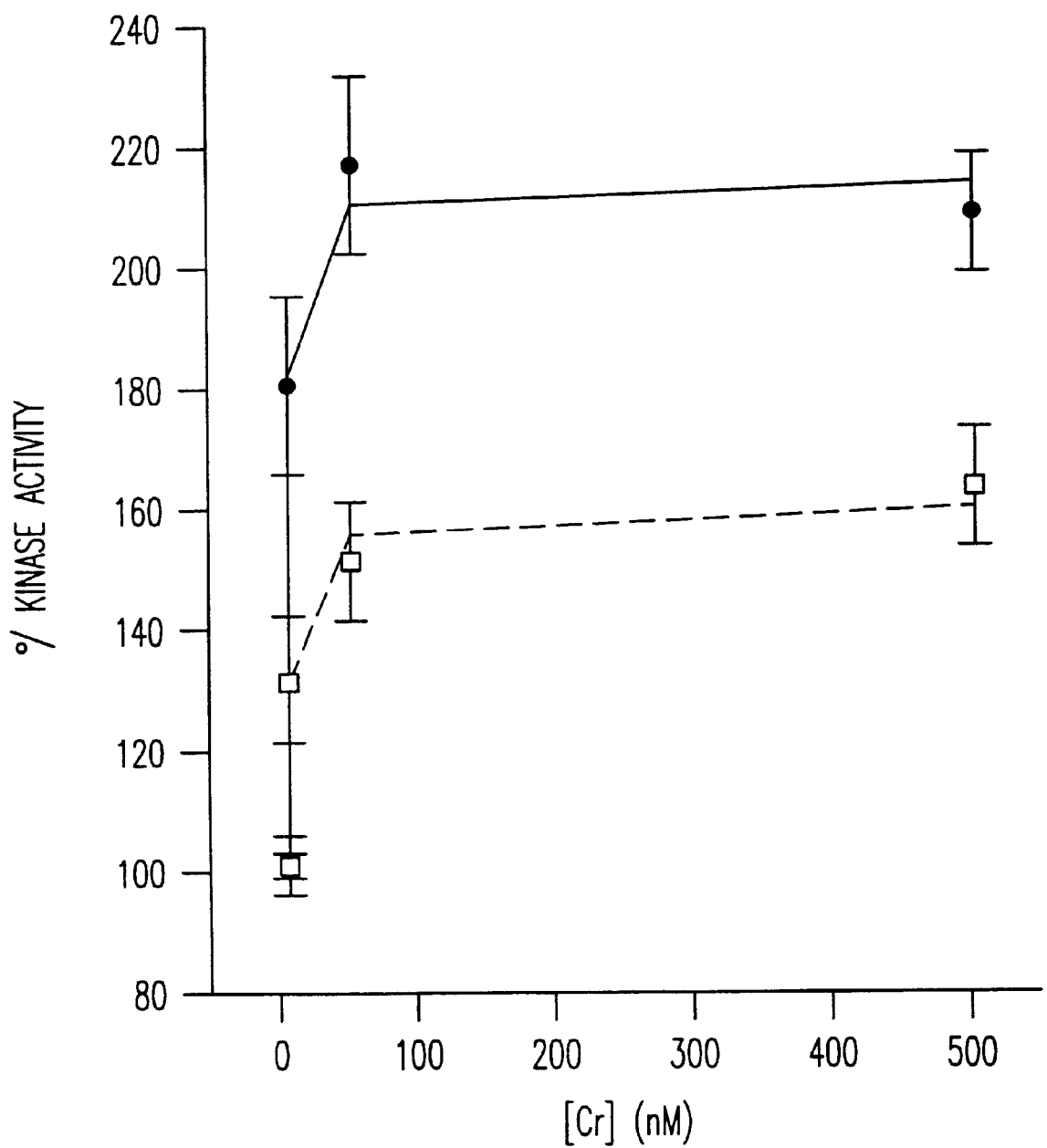
FIG. 2: Activation of rat adipocytic membrane protein tyrosine kinase activity using a fragment of gastrin (0.75 mM) as substrate by LMWCr (solid circles) and by [Cr$_3$O (O$_2$CCH$_2$CH$_3$)$_6$(H$_2$O)$_3$]NO$_3$ (open squares) in the presence of 100 nM IGF-1. 25 µL of rat membrane suspension corresponding to 0.0895 mg protein/mL was utilized. The line is the best fit hyperbolic curve giving a dissociation constant of 507 pM for LMWCr and for [Cr$_3$O (O$_2$CCH$_2$CH$_3$)$_6$(H$_2$O)$_3$]NO$_3$ a dissociation constant of 730 pM.
Figure 3:
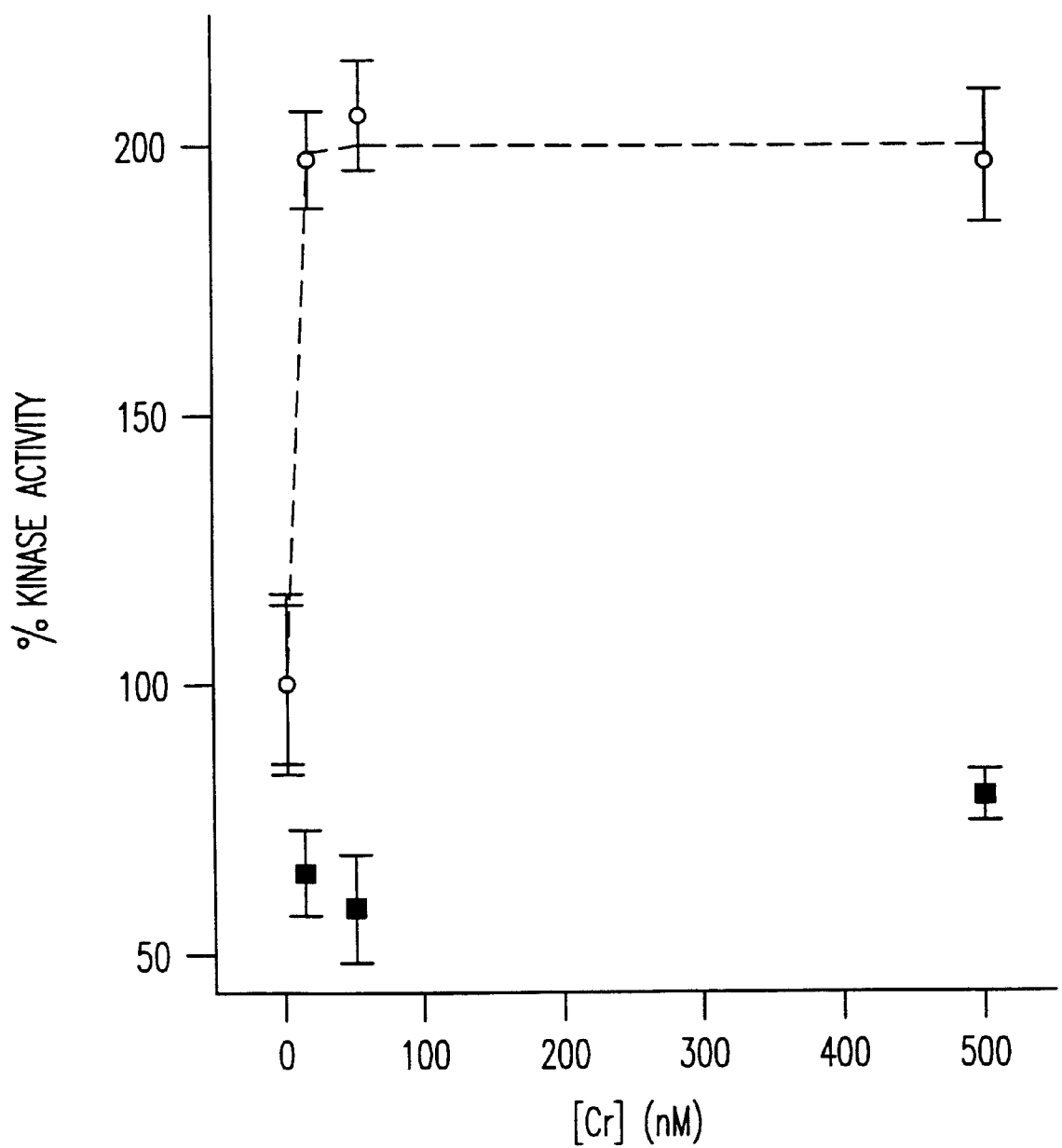
FIG. 3: Activation of rat adipocytic membrane protein tyrosine kinase activity using 0.75 mM gastrin (amino acids 1-17) as substrate by $[Cr_3O(O_2CCH_3)_6(H_2O)_3]Cl$ (solid squares and by $[Cr_3O(O_2CCH_2CH_3)_6(H_2O)_3]NO_3$ (open circles) in the presence of 100 nM insulin. 25 µL of rat adipocyte membrane suspension corresponding to 0.0856 mg of protein/mL was utilized. 100% activity corresponds to insulin-stimulated kinase activity and is typically about 0.338 pmol phosphotyrosine per mg membranes. The line is the best fit hyperbolic curve yielding a dissociation constant of 2.98 nM for $[Cr_3O(O_2CCH_2CH_3)_6(H_2O)_3]NO_3$.
Figure 4:
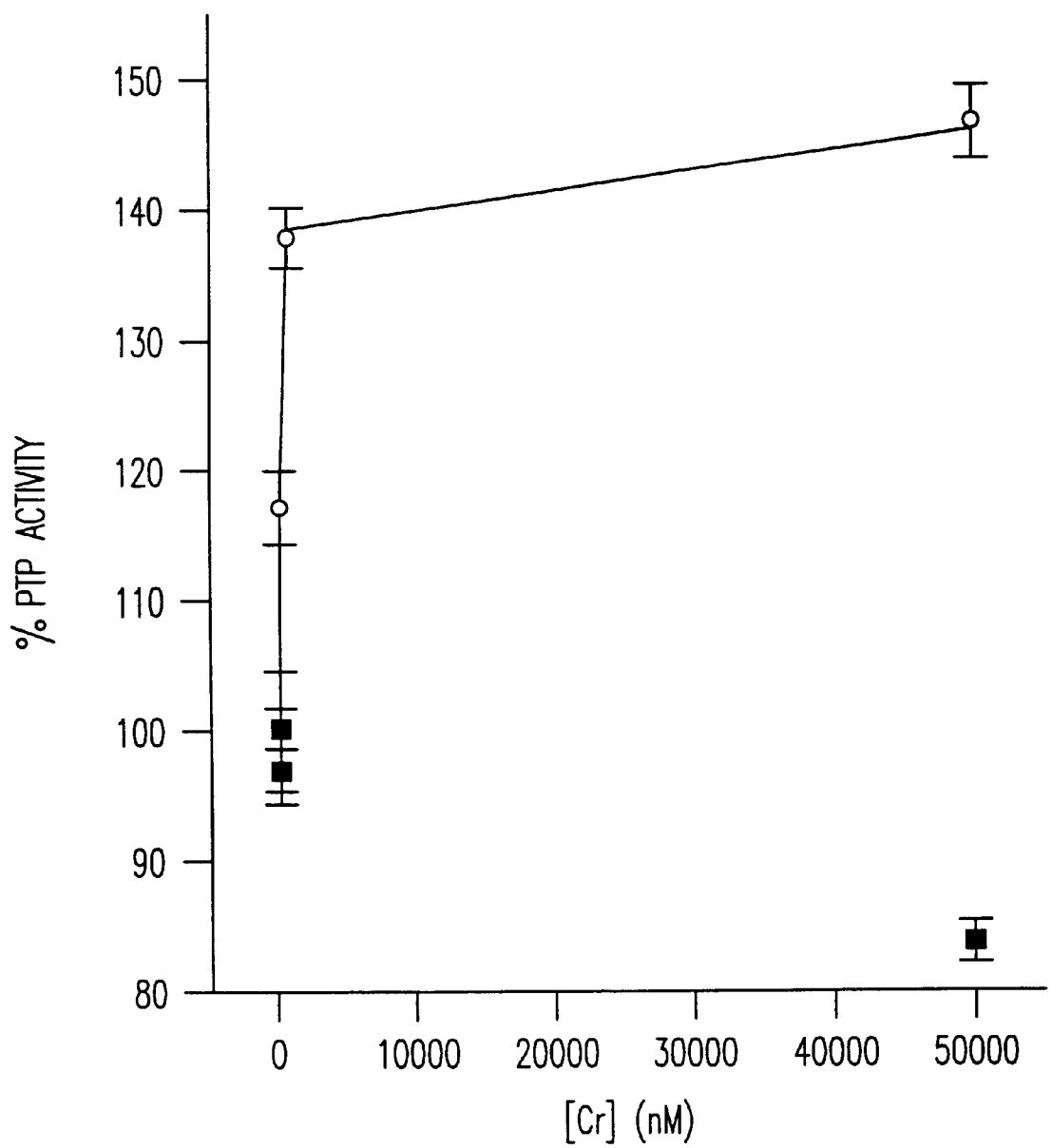
FIG. 4: Activation of rat adipocytic membrane protein phosphatase activity using 5 mM p-NPP as substrate by $[Cr_3O(O_2CCH_3)_6(H_2O)_3]Cl$ (solid squares) and by $[Cr_3O(O_2CCH_2CH_3)_6(H_2O)_3]NO_3$ (open circles). 125 µL of a rat membrane suspension corresponding to 0.0856 mg of protein/mL was utilized. The line is best fit hyperbolic curve yielding a dissociation constant of 30 nM for $[Cr_3O(O_2CCH_2CH_3)_6(H_2O)_3]^+$.

The ability of the synthetic materials to activate membrane phosphotyrosine protein phosphatase activity and insulin-dependent membrane tyrosine protein kinase activity were examined; (LMWCr has previously been shown to also activate a membrane-associated phosphotyrosine phosphatase activity in rat adipocytic membrane fragments).[2] As shown in FIGS. 3 and 4, the acetate triangle 2 does not activate but rather inhibits both the membrane phosphatase and kinase activity. In stark contrast, the propionate analogue (1) results in an activation of both activities in a fashion very similar to LMWCr. The kinase activity is stimulated approximately twofold, while the phosphatase activity is increased nearly 50%. Fitting the curves of FIGS. 3 and 4 to a hyperbolic function results in dissociation constants for the trinuclear species of 2.98 nM and 30 nM for the kinase and phosphatase activities, respectively. These results are strikingly similar to those using LMWCr. LMWCr results in a 250% increase in insulin-dependent tyrosine kinase activity with a dissociation constant of 875 pM[1] (one third that of the model) and a 100% increase in phosphatase activity with a dissociation constant of 4.4 nM$^2$ (one seventh that of the model). Consequently, 1 is an excellent functional model of LMWCr but possesses somewhat less activation while requiring slightly higher concentrations to achieve these affects. To test just how good a model of LMWCr that complex 1 is its ability to activate the active site fragment of the beta subunit of IR and the IGF-1 receptor were also examined (FIGS. 1 and 2). For the IR beta subunit fragment, complex 1 resulted in a circa 60% increase in kinase activity with a dissociation constant of 730 nM; for the IGF-1-dependent membrane kinase activity, an increase of 250% was observed with a dissociation constant of 1.00 nM. In both cases the dissociation constant for the synthetic material is within a order of magnitude of that for LMWCr. Thus, the trinuclear chromic assembly 1 mimics LMWCr in its ability to activate adipocytic membrane phosphotyrosine phosphatase activity, insulin-dependent adipocytic membrane tyrosine protein kinase activity, insulin-like growth factor-1-dependent adipocytic membrane tyrosine protein kinase activity, and the tyrosine protein kinase activity of the active site fragment of the beta subunit of insulin receptor. The ability of LMWCr and complex 1 to activate both protein tyrosine kinases and phosphotyrosine phosphatases may seem paradoxical; however, the stimulation of both types of enzymes appears to be common in complex signal transduction pathways.[34]

To guarantee that the trinuclear cation 1 was the actual active species in solution, the stability of complex in water and in the buffer had to be ascertained. Parmagnetic NMR has been demonstrated to be of utility in characterizing antiferromagnetically-coupled chromium(III) assemblies.[24a–c,33,35] For acetate and propionate ligands bridging between chromic centers in these assemblies, the resonances of methyl hydrogens of acetate and the methylene protons of propionate occur in the +35 to +45 ppm range.[33] The nitrate sale of 1 was dissolved in $D_2O$ and adding a quantity of DC1 equivalent to the quantity of HCl needed to make the same quantity of 50 mM Tris buffer, pH 7.4 in $H_2O$; $^1H$ NMR spectra of 5 mM solutions of 1 were collected every five minutes for two hours. During this period, the integration of the propionate methylene resonances (+42 ppm) were unchanged, and no new signals appeared. Thus, the triangle appears to be stable in aqueous solution and in the assay buffer, and the activation activity can be assigned to the trinuclear cation.

Figure 5:
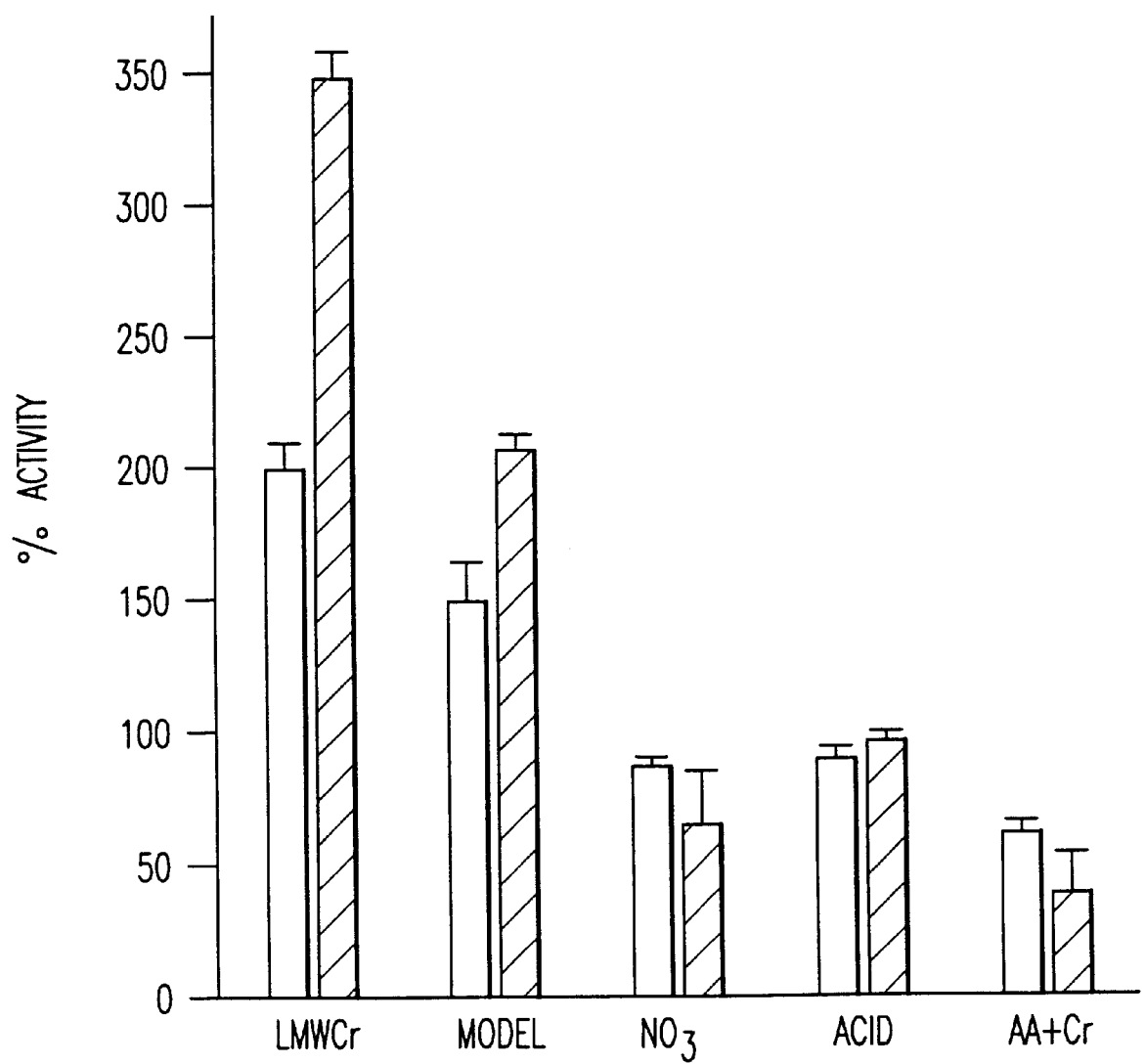
FIG. 5: Influence of chromium complexes (nM) and their components (µM propionate and nM nitrate) on adipocytic membrane tyrosine protein kinase activity in the presence of 100 nM insulin solid bars) and adipocytic membrane phosphotyrosine phosphatase activity (open bars). 100% activity represents the activity in the absence of added chromium complexes or their components. 25 µL of a rat membrane suspension corresponding to 0.0895 mg protein/ml was utilized. For the kinase assays, 50 nM concentrations of LMWCr, complex 1, and the Cr-amino acid mixture (in terms of Cr) were used; 500 nM nitrate and propionate were used. For the phosphatase assays, 50 µM concentrations of LMWCr, complex 1, and the Cr-amino-acid mixture (in terms of Cr) were used; 50 µM nitrate and propionate were used. Model=complex 1; Acid=propionic acid; AA+Cr= chromium amino acid mixture.

Additionally the components of 1 were examined for any ability to potentiate membrane phosphatase activity and insulin-dependent membrane kinase activity (FIG. 5). Propionic acid and nitrate (at concentrations comparable to those if 1 dissociated completely in water) do not potentiate either phosphatase or kinase activity; previously, mononuclear chromic salts were also been shown to not result in potentiation of either activity.[1,2] A mixture of the components of LMWCr was similarly tested for its ability to potentiate these activities. The mixture consisted of chromic ions, aspartate, glutamate, glycine, and cysteine in a 4:2:4:2:2 ratio, corresponding to the approximate ratio of the components in isolated bovine liver LMWCr.[3] At a chromium concentration equivalent to that used for LMWCr in the assays, the mixture actually inhibited kinase and phosphatase activity. Thus, the multi-nuclear chromic complexes 1 and LMWCr appear to be unique in their ability to potentiate membrane phosphotyrosine phosphatase and insulin-dependent membrane kinase activity.

While LMWCr has been proposed for use as a nutritional supplement and in treatment of adult-onset diabetes and related conditions associated with improper carbohydrate and lipid metabolism,[1–3] complex 1 may be even more promising for use in these applications. The synthetic material is prepared from inexpensive reagents[16] (and consequently not requiring a time consuming isolation as with LMWCr), is extremely stable in aqueous solution (LMWCr undergoes a slow hydrolysis),[3] and even stable in acidic solution. The trinuclear basic carboxylates of chromium(III) can, for example, be recrystallized from dilute mineral acids;[15] consequently 1 might readily survive oral ingestion unlike LMWCr. Cation 1 also has a molecular weight of 664 compared to approximately 1480 daltons for bovine liver LMWCr,[3] which should facilitate movement of the former across cell membranes. Curiously, Mirsky and coworkers reported that addition of cations 1 and 2 and $[Cr_3O(O_2CH_6(H_2O)_3]^{+}$ caused a 15–20% enhancement of carbon dioxide production by yeast;[36] the similar behavior of the three cations does not agree with the quite different behavior seen for cations 1 and 2 in this work. Unfortunately, experimental details for the studies with the three cations by Mirsky et al. are lacking, and no data is presented. As a result, it is difficult to determine how the cations might be influencing fermentation and to ascertain the relationship (if any) between the yeast fermentation assay and human glucose and lipid metabolism.

CONCLUSIONS

These studies show that LMWCr and the synthetic analogue $[Cr3O(O_2CCH_2CH_3)_6(H_2O)_3]^{+}$ activate insulin receptor protein tyrosine kinase activity by interacting at or near the kinase active site of the enzyme's beta subunit, while both materials are able to activate protein tyrosine kinase activity of rat adipocytic membrane fragments in response to insulin-like growth factor in addition to insulin and also activate phosphotyrosine phosphatase activity of adipocytic membranes. The similarity between the activation by LMWCr and complex 1 supports the proposal that LMWCr possesses a multinuclear chromic assembly similar to that of complex 1.[3] The mechanism of the activation by the chromium complexes is under investigation, as are the effects of the materials on diabetic animal models.

Obviously, numerous modifications and variations of the present invention are possible in light of the above teachings. It is therefore to be understood that within the scope of the appended claims, the invention may be practiced otherwise than as specifically described herein.

REFERENCES (1) Davis, C. M.; Vincent, J. B. Biochemistry 1997, 36,4382.
(2) Davis, C. M.; Sumrall, K. H.; Vincent, J. B. Biochemistry 1996, 35, 12963.
(3) Davis, C. M.; Vincent, J. B. Arch. Biochem. Biophys. 1997, 339,335.
(4) Morris, B. W.; Blumsohn, A.; McNeil, S.; Gray, T. A. Am. J. Clin. Nutr. 1992, 55, 989; Morris, B. W.; Gray, T. A.; MacNeil, S. Clin. Sci. 1993, 84,477; Morris, B. W.; MacNeil, S.; Stanley, K.; Gray, T. A.; Fraser, R. J. Endocrin. 993, 139,339.
(5) Yamamoto, A.; Wada, O.; Ono, T. Eur. J. Biochem. 1987, 165, 627.
(6) Yamamoto, A.; Wada, O.; Ono, T. J. Inorg. Biochem. 1984, 22, 91.
(7) Mertz, W.; Roginski, E. E.; Schwartz, K. J. Biol. Chem. 1961, 236, 318; Mertz, W.; Roginski, E. E. J. Biol. Chem. 1963, 238, 868; Mertz, W. J. Nutr. 1993, 123, 626; Vincent, J. B. In Encyclopedia of Inorganic Chemistry; King, B., Ed.; John Wiley: New York, 1994; Vol. 2, pp 661–665.
(8) Anderson, R. A. Biol. Trace Elem. Res. 1992, 32, 19.
(9) Anderson, R. A.; Cheng, N.; Bryden, N.; Polansky, M.; Cheng, N.; Chi, J.; Feng, J. Diabetes 1996, 45, Suppl. 2, 124A.
(10) Ravina, A.; Slezack, L. Harefuah 1993, 125, 142.
(11) Stearns, D. M.; Wise, J. P., Jr.; Patiermo, S. R.; Wetterhahn, K. E. FASEB J. 1995, 9, 1643.
(12) McCarty, M. F. J. Opt. Nutr. 1993, 2, 36; Vincent, J. B. J. Nutr. 1994, 124, 117.
(13) Anderson, R. A.; Kozlovsky, A. S. Am. J. Clin. Nutr. 1985, 41, 1177; Anderson, R., A.
In Risk Assessment of Essential Elements; Mertz, W., Abernathy, C. O., Olin, S. S., Eds.; ISLI Press: Washington, 1994: pp 187–196.
(14) Sumrall, K. H.; Vincent, J. B., Polyhedron 1997, 16, 4171.
(15) Johnson, M. K.; Powell, D. B.; Cannon, R. D. Spectrochim. Acta 1981, 37A, 995, incorporated herein by reference.
(16) Earnshaw, A.; Figgis, B. N.; Lewis, J. J. Chem. Soc. (A) 1966, 1656, incorporated herein by reference.
(17) Undenfriend, S.; Stein, S.; Bohlen, P.; Dairman, W.; Leimgruber, W.; Weigele, M. Science 1972. 178, 871.
(18) Marczenko, Z. Spectrophometric Determination of the Elements Ellis Horwood: Chichester, England, 1986.
(19) Rodbell, M. J. Biol. Chem. 1964, 239, 375.
(20) Anderson, R. A.: Brantner, J. H.; Polansky, M. M. J. Agric. Food Chem. 1978, 26, 1219.
(21) Li, J.; Elberg, G.; Gefel, D.; Shechter, Y Biochemistry 1995, 34, 6218.
(22) Lee, J.; Pilch, P. F. Am. J. Physiol. 1994, 35, C319; White, M. F.; Kahn, C. R. J. Biol. Chem. 1994, 269, 1.
(23) Hedlin, C. -H. Cell 1995, 80,213.
(24) (a) Harton, A.; Nagi, M. K.; Glass, M. M.; Junk, J. L.; Atwood, J. L.; Vincent, J. B. Inorg. Chim. Acta 1994, 217, 171; (b) Ellis, T.; Glass, M.; Harton, K.; Huffman, J. C.; Vincent, J. B. Inorg. Chem. 1994, 33, 5522; (c) Nagi, M. K.; Harton, A.; Donald, S.; Lee, Y. S.; Sabat, M.; O'Connor, C. J.; Vincent, J. B. Inorg. Chem. 1995, 34, 3813; (d) Bino, A.; Chayat, R.; Pederson, E.; Schneider, A. Inorg Chem. 1991, 30, 856; (e) Donald, S.; Terrell, K.; Vincent, J. B.; Robinson, K. D. Polyhedron 1995, 14, 971.
(25) Cannon, R. D.; White, R. P. Prog. Inorg. Chem. 1988, 36, 195.
(26) Weinland, R. F.; Hoehn, K. Z. Anorg. Chem. 1911, 69, 158.
(27) Weinland, R. F.; Lindner, J. Z. Anorg. Chem. 1930, 190, 285.
(28) Szynanska-Buzar, T.; Ziolkowski, J. J. Sov. J. Coord. Chem. 1976, 2, 897; Zelentsov, V. V.; Zhemchuzhikova, T. A.; Rakitin, Yu. V.; Yablokov, Yu. V.; Yakubov, Kh. M.. Koord. Khim. 1975, 1, 194; Yoshida, T.; Morita, M.; Date, M. J. Phys. Soc. Jpn. 1988, 57, 1428.
(29) Morita, M.; Kato, Y. Inter, J. Quantum Chem. 1980, 18, 625.
(30) Antsyshkina, A. S.; Porai-Koshits, M. A.; Arkhangel'skii, I. V.; Diallo, I. N. Russ. J. Inorg. Chem. 1987, 32, 1700.
(31) Hondo, M.: Morita, M.; Datae, M. J. Phys. Cos. Jpn. 1992, 61, 3773; Nishimura, H; Date, M. J. Phys. Jpn. 1985, 54, 395.
(32) Fu, G.; Yu, L.; Zhu, Z.; Xie, W.; Zheng, Y.; Zhang, L. Jiegou Huaxue 1990, 4, 278: van den Bergen, A.; Colton, R.; Percy, M.; West, B. O. Inorg. Chem. 1993, 32, 3408.
(33) Glass, M. M.; Belmore, K.; Vincent, J. B. Polyhedron 1993, 12, 133.
(34) Hunter, T. Cell 1995, 80, 225.
(35) Vincent, J. B. Inorg. Chem. 1994; 33, 5604; Belmore, K.; Madison, X. J.; Harton, A.; Vincent, J. B. Spectrochim. Acta 1994, 50A, 2365.
(36) Mirsky, N.; Weiss, A.; Dori, Z. J. Inorg. Biochem. 1980, 13, 11.

What is claimed is:

1. A pharmaceutical composition, comprising:
   (a) a chromium(III) complex represented by the formula $[Cr_3O(O_2CCH_2CH_3)_6(H_2O)_3]^+$; and
   (b) at least one additional pharmaceutical agent.

2. The composition of claim 1, wherein the additional pharmaceutical agent is an anti-diabetes agent.

3. The composition of claim 1, wherein the anti-diabetes agent is insulin.

4. The composition of claim 1, which is in the form of a tablet, capsule or caplet.

5. The composition of claim 1, which is in the form of a solid.

6. The composition of claim 1, which is in the dosage form of a tablet, a capsule, or a caplet, and the dosage form contains 5 to 600 mcg of chromium.

7. The composition of claim 1, which further comprises at least one pharmaceutically acceptable excipient.

8. The composition of claim 1, which further comprises at least one pharmaceutically acceptable excipient selected from the group consisting of disintegrators, binders, and lubricants.

9. A method of treating diabetes, comprising administering an effective amount of the composition of claim 2 to a patient in need thereof.

10. The method of claim 9, wherein the anti-diabetes agent is insulin.

* * * * *